(12) United States Patent
Egli et al.

(10) Patent No.: US 9,273,956 B2
(45) Date of Patent: Mar. 1, 2016

(54) METHOD FOR DETERMINING A DISTANCE BY X-RAY IMAGING, AND X-RAY DEVICE

(71) Applicant: SIEMENS AKTIENGESELLSCHAFT, Munich (DE)

(72) Inventors: Adrian Egli, Sursee (CH); Adrian John, Kaisten (CH); Gerhard Kleinszig, Forchheim (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 159 days.

(21) Appl. No.: 13/935,835

(22) Filed: Jul. 5, 2013

(65) Prior Publication Data

US 2014/0016743 A1 Jan. 16, 2014

(30) Foreign Application Priority Data

Jul. 5, 2012 (DE) .......................... 10 2012 211 742

(51) Int. Cl.
*A61B 6/02* (2006.01)
*G01N 23/04* (2006.01)
*G01B 15/00* (2006.01)

(52) U.S. Cl.
CPC ................ *G01B 15/00* (2013.01); *A61B 6/022* (2013.01); *G01N 2223/414* (2013.01)

(58) Field of Classification Search
CPC ................ A61B 6/5241; A61B 6/022; G01N 2223/414; G01C 11/06; G06T 7/0075; G06T 2207/10012
See application file for complete search history.

(56) References Cited

U.S. PATENT DOCUMENTS

| | | | |
|---|---|---|---|
| 4,099,880 A | 7/1978 | Kano | |
| 7,394,946 B2 | 7/2008 | Dewaele | |
| 8,126,111 B2 * | 2/2012 | Uhde et al. | ........................ 378/41 |
| 8,699,670 B2 * | 4/2014 | Graumann et al. | ............ 378/162 |
| 2006/0239528 A1 | 10/2006 | Camus et al. | |

FOREIGN PATENT DOCUMENTS

| | | |
|---|---|---|
| CN | 1737810 A | 2/2006 |
| CN | 1864646 A | 11/2006 |
| DE | 10 2005 018 327 A1 | 10/2006 |
| DE | 10 2007 034 221 A1 | 4/2008 |
| EP | 1 598 778 A1 | 11/2005 |
| EP | 1 632 181 A1 | 3/2006 |
| JP | H10132516 A | 5/1998 |

* cited by examiner

*Primary Examiner* — Glen Kao
*Assistant Examiner* — Dani Fox
(74) *Attorney, Agent, or Firm* — Laurence Greenberg; Werner Stemer; Ralph Locher

(57) ABSTRACT

A method for determining a distance between a first point and a second point on an object under examination inside the body of a person under examination by way of x-ray imaging by an x-ray device. The method includes the recording of x-ray images at different relative positionings of the x-ray device, which contain the first and the second point respectively. The relative positionings are substantially shifted in relation to one another in parallel to a central beam. Stereo reconstruction is carried out to define a 3D position of the first point and of the second point. The distance between the first point and the second point is determined from the 3D position of the first point and the 3D position of the second point.

12 Claims, 6 Drawing Sheets

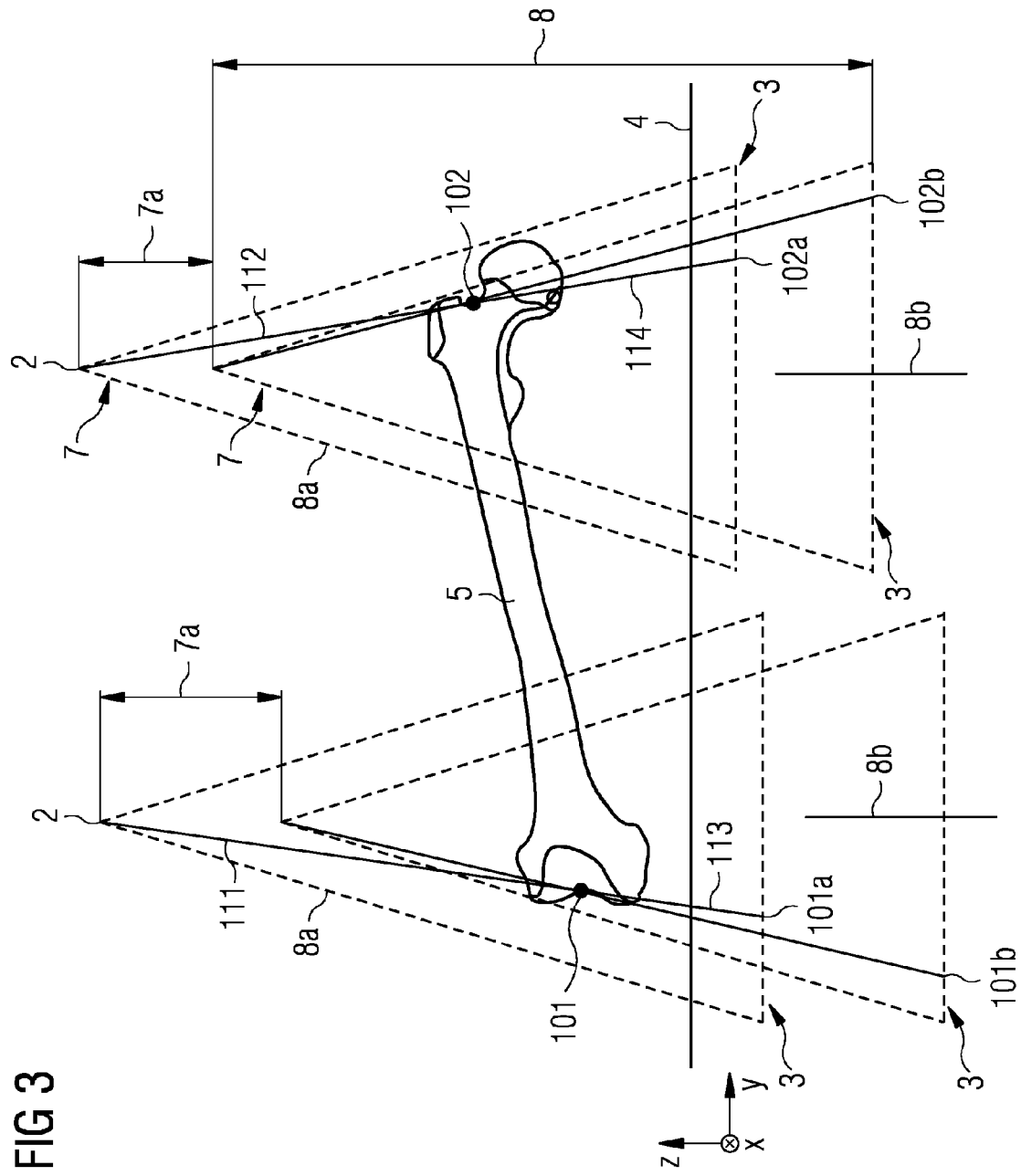

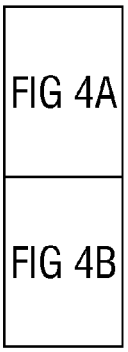
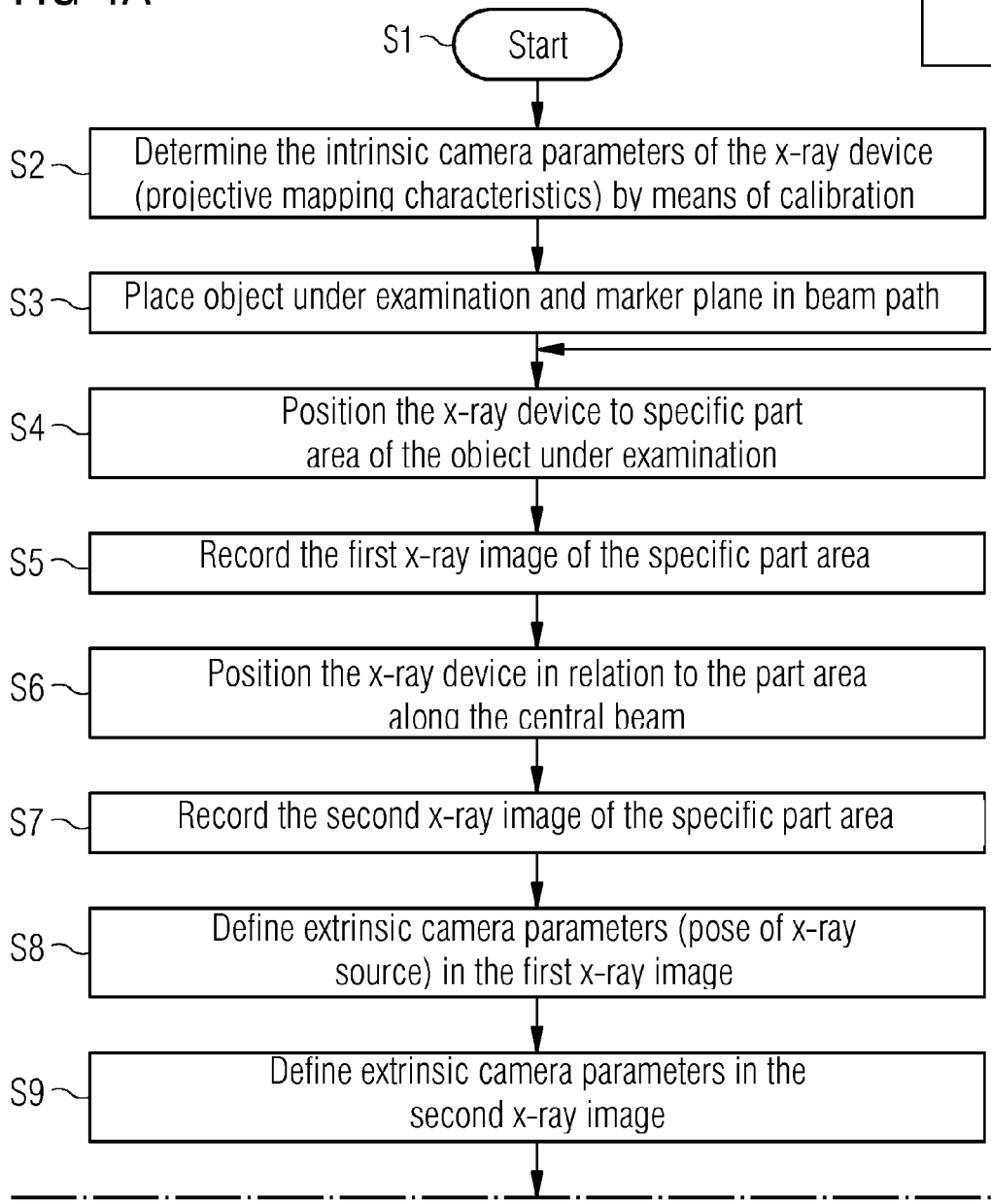

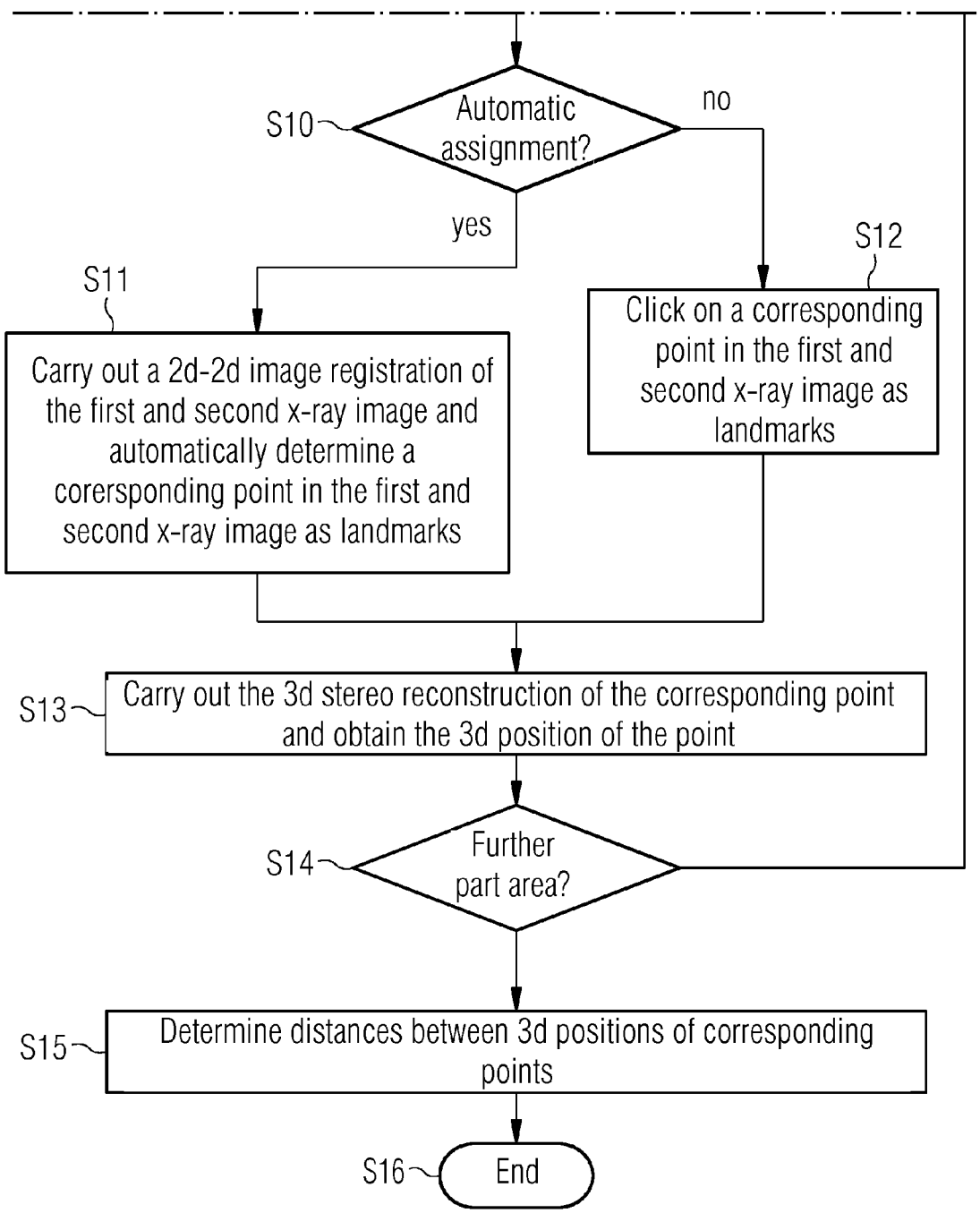

METHOD FOR DETERMINING A DISTANCE BY X-RAY IMAGING, AND X-RAY DEVICE

CROSS-REFERENCE TO RELATED APPLICATION

This application claims the priority, under 35 U.S.C. §119, of German patent application DE 10 2012 211 742.3, filed Jul. 5, 2012; the prior application is herewith incorporated by reference in its entirety.

BACKGROUND OF THE INVENTION

Field of the Invention

The invention relates to a method for determining a distance between a first point and a second point on an object under examination within the body of a person under examination by way of x-ray imaging. The invention also relates to an x-ray device. In particular the invention relates to techniques for stereo reconstruction of the first and the second point for obtaining a three-dimensional position in each case of the first and second point in relation to an x-ray source of the x-ray device.

X-ray imaging, for example by way of a C-arm x-ray device, allows images or measurement data of an object under examination to be detected from inside the body of a person under examination. Such images can serve as a foundation for a later and separate medical application, but physical measurement variables can also be determined from the images. The measurement variables can especially relate to volumes and/or distances, axes and angles.

For a wide diversity of techniques such measurement variables must be determined manually by medical personnel. However even with automatic or processor-based determination of these measurement variables a metric distance determination, i.e. length determination, is only possible to a limited extent or is very much subject to errors, since with so-called long objects a restricted visibility of the objects in the x-ray imaging occurs. Conventional C-arm devices can namely typically have a resolution or a field of view which do not allow or only allow the object under examination to be visualized to a restricted extent or allow data to be detected for the entire object under examination.

Techniques used for this purpose are known in literature, which allow a plurality of detected images to be combined into one overall image, i.e. what is referred to as mosaicing/stitching approaches (image mosaic techniques). Such a method and a system for image composition is known for example from European published patent application EP 1 632 181 A1, especially for x-ray images recorded with a C-arm device. On the basis of location marks of a marker plane recorded at the same time, a plurality of part images can be combined into one overall image. The absolute position within the marker plane, which can be determined from the location marks, can be detected automatically by way of data processing methods and the part images can be merged in this way into an overall image.

However such techniques can have certain disadvantages. For example the location marks can be applied not just to the object under examination itself but to a separate marker plane—the marker plane can especially have an offset and/or a tilt in relation to the object under examination. The merging or the image composition is then carried out not with reference to the object under examination itself, but with reference to the location markers offset for example in the longitudinal direction (i.e. in the direction of a central beam of the x-ray device and at right angles to the detector plane for example). Formulated in more abstract terms, it can occur for example that it is not the object under examination that is measured but the help object of the location markers. This can, inter alia with regard to the projective imaging properties of the C-arm device, cause an imprecision in the image composition, so that an uncertainty or an error in measured values derived from the overall image, such as distances, results.

There is therefore a need to provide better techniques for determining distances in x-ray imaging.

SUMMARY OF THE INVENTION

It is accordingly an object of the invention to provide an x-ray processing method and an x-ray device which overcome the above-mentioned disadvantages of the heretofore-known devices and methods of this general type and which provide for an advantageous process for determining distances in x-ray imaging.

With the foregoing and other objects in view there is provided, in accordance with the invention, a method for determining a distance between a first point and a second point on an object under examination within the body of a person under examination by x-ray imaging with an x-ray device, the method which comprises:

recording a first x-ray image containing the first point, with a first relative positioning of an x-ray source to the object under examination;

recording a second x-ray image containing the first point, with a second relative positioning of the x-ray source to the object under examination;

wherein the first relative positioning and the second relative positioning are shifted relative to one another substantially in parallel to a central beam of the x-ray device;

recording a third x-ray image containing the second point, with a third relative positioning of the x-ray source to the object under examination;

recording a fourth x-ray image containing the second point, with a fourth relative positioning of the x-ray source to the object under examination;

wherein the third relative positioning and the fourth relative positioning are shifted relative to one another substantially in parallel to the central beam of the x-ray device;

determining a location of the first point in the first x-ray image and in the second x-ray image;

determining a location of the second point in the third x-ray image and in the fourth x-ray image;

carrying out a stereo reconstruction based on the locations of the first point thus determined as a corresponding landmark for obtaining a 3D position of the first point;

carrying out a stereo reconstruction based on the locations of the second point thus determined as a corresponding landmark for obtaining a 3D position of the second point; and determining the distance between the first point and the second point from the 3D position of the first point and the 3D position of the second point.

In other words, in accordance with one aspect the invention relates to a method for determining a distance between a first point and a second point on an object under examination within the body of a person under examination by means of x-ray imaging by an x-ray device, wherein the method comprises the recording of a first x-ray image which contains the first point with a relative positioning of an x-ray source to the object under examination. The method further comprises the recording of a second x-ray image which contains the first point with a second relative positioning of the x-ray source to the object under examination. The method further comprises the recording of a third x-ray image which contains the second point with a third relative positioning of the x-ray source to the object under examination. The method further comprises the recording of a fourth x-ray image which contains the second point, with fourth a relative positioning of the x-ray source to the object under examination. The method further comprises the definition of a position of the first point in the first x-ray image and in the second x-ray image and the definition of a position of the second point in the third x-ray image and the fourth x-ray image. The method further comprises the execution of a stereo reconstruction based on the specific positions of the first point as a corresponding landmark for obtaining a three-dimensional (3D) position of the first point, as well as the execution of a stereo reconstruction based on the specific positions of the second point as a corresponding landmark for obtaining a 3D position of the second point. The method further comprises the definition of the distance between the first point and the second point from the 3D position of the first point and the 3D position of the second point. The first relative positioning and the second relative positioning are essentially offset in relation to each other in parallel to a central beam of the x-ray device and the third relative positioning and the fourth relative positioning are essentially offset in relation to one another in parallel to the central beam of the x-ray device.

It is possible, for example, for the 3D position of the first point and the second point to be defined or specified in a reference system. By way of example, the reference coordinate system can be defined by location marks in a marker plane, e.g. on a marker object which is located in the beam path of the x-rays. In other words it can be possible for the first and second and third and fourth x-ray images to map location marks of a location-encoded marker plane, wherein the 3D position of the first point and the 3D position of the second point are determined in a reference coordinate system of the location marks. It is also possible to use an x-ray device navigation device which monitors the relative positionings of the x-ray device and determines the reference coordinate system. It should be understood that it can be sufficient to determine the 3D position of the first and second point in one and the same reference coordinate system. It can then namely be possible to determine the distance directly from the two 3D positions—how accurately the reference coordinate is defined can be of no significance in this case.

For example the x-ray device can be a C-arm device or a permanently installed x-ray device. For example the x-ray device can comprise an x-ray source and an x-ray detector, which for example are disposed at a fixed distance from one another, e.g. in parallel to a central beam of the x-ray photons. This fixed distance can designate a focal point, extend along with the central beam and therefore define a longitudinal direction. Therefore the longitudinal direction can be defined as a direction which is oriented along or in parallel to a beam path of the central beam of x-ray photons.

Stereo reconstruction is a technique generally known to the person skilled in the art. This can allow the determination of the 3D position of corresponding landmarks in relation to the camera position, which are determined in at least two two-dimensional (2D) images. Details of this technique do not have to be explained further here since they are known to the person skilled in the art.

The relative positions essentially shifted in parallel to the central beam can for example have the following meanings: Shifting in relation to the central beam, shifting by an error angle of less than 5° or less than 10°. In particular the error angle can be restricted by maximum acceptable transformation parameters (such as compression, rotation, etc.), except for scaling.

The distance between the first point in the second point can be broken down into components in the longitudinal direction and the vertical direction, i.e. in parallel to and perpendicular to the central beam. It can for example be possible, by comparison with the conventional methods described above which are based on location encoding of location marks in a marker plane, to achieve improved accuracy in the determination of the distance. This can especially be the case by taking into account all three dimensions and in determining the distance. By taking into account the 3D positions in the calculation of the distance between the first point in the second point a higher accuracy can be obtained in the calculation. This can reduce an uncertainty in the determination of the physical measured variable "distance", which can be of great importance in the technical application. Subsequent and separate medical applications can also be carried out more accurately and more safely in this way. The distance can be used for further geometrical parameters, such as angles, etc.

The first and second x-ray image can map a first part area of the object under examination and have different imaging scales and/or not be rotated and tilted in relation to one another or only slightly rotated and tilted. The third and fourth x-ray image can also only map a second part area of the object under examination and have different imaging scales and not be tilted or only be slightly tilted in relation to one another. In other words the first part area can therefore include the first point and the second part area can include a second point.

Typically the beam path of the x-ray photons can spread out for increasing distances to the x-ray source. As a result of this spreading out of the cross section of the beam path, i.e. the diverging beam path, a different height setting of the x-ray device, i.e. a different positioning of the object under examination in parallel to the central beam can cause a change in the imaging scale of the imaged objects. For example objects which are located closer (further away) from the x-ray source can be recorded larger (smaller) in the x-ray images. In other words the imaging scale can be different for different height settings.

The focal length of the x-ray device, e.g. especially of the C-arm device, can be determined for example by an opening angle of the beam path and a surface of the x-ray detector. Purely illustratively and not limiting a focal length of the C-arm device of 1 m, as a result of the spreading out of the cross beam section, can for example mean a beam cross-section of around 0.23 m at 1 m distance to the x-ray beam source (11° opening angle). For example a typical distance between the x-ray source and the x-ray detector can amount to 1 m.

By way of example, the first and second relative positioning or the third and fourth relative positioning can correspond to different height settings (relative positionings of the object under examination along the central beam, i.e. in the longitudinal direction, in relation to the x-ray source) of the x-ray device, i.e. have a different arrangement of the object under examination in the beam path of the x-ray photons, e.g. be closer to or further away from the x-ray source. In this way—e.g. even with a fixed focal length of the x-ray device—it can be achieved that essentially the imaging scale between the first and the second or the third and the fourth x-ray image changes. E.g. the rotation and tilting can be kept constant within the framework of the positioning accuracy of the x-ray device. In this way especially the positions of the first and second point in the respective images can be determined especially simply, since the respective x-ray images—except for the imaging scale—match one another to a great extent.

In general the first and second relative positioning or the third and fourth relative positioning correspond to different relative positions along the beam path.

Typical x-ray devices, especially C-arm devices, can have a fixed distance between the x-ray source and the x-ray detector. However it should be understood that the relative positioning can be equivalently achieved by a change in the positioning of the x-ray source and/or the x-ray detector in relation to the e.g. fixed object under examination—or by a change in the positioning of the object under examination in relation to the fixed x-ray source and x-ray detector. A decisive factor can especially be a relative positioning between the x-ray source and the x-ray detector on the one hand and the object under examination on the other hand.

The first and second relative positioning can be offset from one another in relation to the third and fourth relative positioning essentially at right angles to a central beam of the x-ray device. This can mean for example that the first and second part area are primarily shifted at right angles to the central beam in relation to one another. It should be understood that the first and second part area of the object under examination mapped by the respective first and second or third and fourth x-ray images must not, even partly, overlap. However the first and second part area can partly overlap. E.g. it can be possible for the first and the second x-ray image to map the first point at a proximal end of the object under examination, e.g. a longitudinal bone, while the third and fourth x-ray image map the second point at a distal end of the longitudinal bone. It is for example not necessary to record the part areas of the object under examination which lie between the first and second point by means of further x-ray images.

In general there can be any given repositioning between the first and the second relative positioning and the third and the fourth relative positioning. The repositioning can be generally known. It is possible to determine the repositioning, e.g. by means of a suitable x-ray device navigation device. Such an x-ray device navigation device can define the reference coordinate system.

In various embodiments it can be possible for the recording of the third x-ray image to correspond to the recording of the first x-ray image and for the recording of the fourth x-ray image to correspond to the recording of the second x-ray image. In other words the first x-ray image can be the same as the third x-ray image and the second x-ray image can be the same as the fourth x-ray image; therefore the first relative positioning can also be the same as the third relative positioning and the second relative positioning the same as the fourth relative positioning. This can be the case if for example the first and second x-ray image already contain the second point. Then the steps of recording the third and fourth x-ray image can already be implemented by the steps of recording the first and second x-ray image. The distance between the first and second point can then be determined within a set of first and second (or third and fourth) x-ray images.

It can be possible for example for the first relative positioning and the third relative positioning to have a first height setting of the x-ray device and for the second relative positioning in the fourth relative positioning to have a second height setting of the x-ray device, wherein the first and second height setting of the x-ray device each designate a different distance between the x-ray source and the object under examination, e.g. along the beam path. It can also be possible for the first and second relative positioning and the third and fourth relative positioning to have the same positioning at right angles to the central beam of the x-ray device. This can allow an especially simple determination of the locations of the first and second point.

By way of example, the locations of the first point and the locations of the second point can be determined manually by the user of the x-ray device. E.g. the user can click on the first and second point in each case in the first and second or third and fourth x-ray image, i.e. in the mapped first or second part area. The user can for example orient themselves on the basis of imaged anatomical information. In particular in an advantageous way just one imaging scale can differ between the first and the second or third and fourth x-ray image, which can make especially simple manual orientation possible.

By way of example, a user interface can be provided which makes it possible for the user, in a visualization of the first and second x-ray image or of the third and fourth x-ray image, to select the first or second point, e.g. by clicking on it. This can explicitly allow distances between anatomically significant points of the object under examination, e.g. proximal or distal ends of a bone, etc., to be made possible. It can also be possible to automatically or partly automatically determine the first point and the second point: e.g. anatomically-relevant points can be identified, etc.

The locations of the first point and the locations of the second point can also be determined at least partly automatically by a 2D-2D image registration of the first x-ray image with the second x-ray image, as well as of the third x-ray image with the fourth x-ray image. Techniques of 2D-2D image registration are known to the person skilled in the art, which can allow an assignment to be established between two 2D images by a transformation. The transformation can especially be a rotation, compression/stretching, scaling, etc. This can make it possible to provide corresponding pairs of first or second points in the first and second or third and fourth x-ray images. In such cases the image registration can serve in each case to bring the first and second or third and fourth x-ray images into the best possible match by application of image transformations. In other words the 2D-2D image registration can quantify differences between the respective x-ray images. In particular the different parameters of the image transformations, e.g. rotation, compression, scaling, etc., can be obtained as the result of the 2D-2D image registration. A wide diversity of methods for 2D-2D are known to the person skilled in the art, so that further details of said methods do not need to be explained.

It can be possible for the user to determine the first (second) point merely either in the first (third) or in the second (fourth) x-ray image—based on the 2D-2D image registration the first or second point can then be determined in the associated x-ray image. But it can also be possible in this way to determine the first and second point fully automatically, e.g. in each case as the furthest proximal and distal assigned point or as another anatomically-relevant point.

In accordance with the methods discussed above the three-dimensional (3D) distance between the first and the second point can be provided. E.g. the distance can be provided with a measurement accuracy or a significance level which is obtained from the corresponding parameters of the 2D-2D image registration. In especially preferred embodiments the first and the second or the third and fourth relative positioning can merely be characterized by different height settings of the x-ray device; i.e. since the object under examination for example was only shifted in parallel to the central beam, only one imaging scale changes. This can mean that the transformation determined in the 2D-2D image registration between the first and second or third and fourth x-ray image only has one scaling, but no or only slight rotation and tilting. This can increase the accuracy of the 2D-2D image registration, or can reduce an uncertainty of the 2D-2D image registration. E.g. it can be possible, as a general condition of the 2D-2D image registration, to determine only the scaling factor of the x-ray image pairs as being not equal to zero.

For stereo reconstruction extrinsic camera parameters, i.e. a pose (position and orientation) of the camera, i.e. here of the x-ray source, can be determined, in the reference coordinate system for example (such as in relation to a location-encoded marker plane); intrinsic camera parameters, i.e. projective imaging properties which for example describe the mapping of a 3D object into a 2D object can also be determined. Techniques are discussed below which allow an especially precise determination of the extrinsic and/or intrinsic camera parameters. This can make it possible to increase an accuracy of the stereo reconstruction and thus the determination of the distance.

For example the method can comprise the determination of extrinsic camera parameters for stereo reconstruction which describe a 3D position and an orientation of the x-ray source in the first and second and third and fourth relative positioning, wherein the execution of the stereo reconstruction takes into account the specific extrinsic camera parameters.

The 3D position and orientation can be determined in the reference coordinate system. E.g. the reference coordinate system can be defined by location marks.

In this case the first and the second and the third and the fourth x-ray image can each map location marks of a location-encoded marker plane, wherein the extrinsic camera parameters are determined on the basis of the mapped location marks.

The location marks can be arranged in a fixed grid and each indicate an absolute positioning within the corresponding reference coordinate system of the marker plane. The absolute positioning of an imaged location mark can be able to be read out electronically. Preferably for this purpose two or more location marks can be mapped per x-ray image. The location marks can also have a known measurement and geometry. The marker plane can for example be defined on a marker object, such as on a flat map, which contains the location marks in printed form or with high contrast in the x-ray imaging. The marker object can then be able to be found during the recording in the beam path, preferably in such a way that the marker plane lies at right angles to the central beam. In other words the central beam can be parallel or essentially parallel to a plane normal of the marker plane. However a specific, preferably small error angle can exist in relation to this alignment. E.g. the marker object can be laid on the table on which the person under examination is located.

Based on the local encoding of the location marks the pose of the x-ray source can be determined absolutely, e.g. in relation to a reference coordinate system which is defined by the marker plane or the location marks.

It is also possible for the determination of the extrinsic camera parameters to be undertaken on the basis of a monitoring of a positioning of the x-ray device between the different relative positionings. E.g. an x-ray device navigation device can be provided which measures a positioning of the components of the x-ray device, i.e. for example the x-ray source and the x-ray detector, as well as the object under examination. Then the relative positionings can be measured. The x-ray device navigation device can also determine the reference coordinate system. The x-ray device navigation device can especially follow the movement of the x-ray source and/or the x-ray detector.

It can then be possible, based on the location information from the monitoring of the positioning of the x-ray device, to determine absolutely the pose of the x-ray source, e.g. in relation to the reference coordinate system which for example can also be defined by a (reference) zero position of the x-ray source.

It can be possible to determine the extrinsic camera parameters both based on the location marks and also based on the monitoring of the positioning, e.g. by averaging the results of these methods. This can further increase the accuracy of the determination.

The method can also include the recording of at least two calibration x-ray images, which in each case map location marks of a location-encoded marker plane. In this case the at least two calibration x-ray images can be recorded with different orientations of the x-ray source to the marker plane. The method can further include the determination of intrinsic camera parameters for stereo reconstruction, which describe imaging properties of the x-ray device from the calibration x-ray images on the basis of the mapped location marks, wherein the execution of the stereo reconstruction takes into account the specific intrinsic camera parameters.

For example the calibration x-ray images can be recorded in a calibration routine before the actual recording of the x-ray images. In general an accuracy of the intrinsic camera parameters determined can be increased with a larger number of recorded calibration x-ray images, and thereby the stereo reconstruction or the distance.

The intrinsic camera parameters can also already be stored in advance and held on the device-specific basis.

The marker plane and the location marks can correspond to those discussed above in relation to the determination of the extrinsic camera parameters. From the known actual geometry of the location marks and the marker plane, it can then be possible, by a comparison with the mapped geometry of the location marks in the recorded calibration x-ray images, to determine the intrinsic camera parameters.

It is also possible for at least one of the at least two calibration x-ray images to be the first x-ray image and/or the second x-ray image and/or the third x-ray image and/or the fourth x-ray image. This can be the case in particular if the x-ray images contain the location marks, e.g. for determining the extrinsic camera parameters.

In accordance with a further aspect the invention relates to a method for determining a distance between a first point and a second point on an object under examination within the body of a person under examination by means of x-ray imaging by an x-ray device, wherein the method comprises: Recording a first x-ray image which contains the first point and the second point for a first relative positioning of an x-ray source, in relation to the object under examination; recording a second x-ray image which contains the first point and the second point for a second relative positioning of an x-ray source in relation to the object under examination; determining a location of the first point in the first x-ray image and in the second x-ray image; determining a location of the second point in the third x-ray image and the fourth x-ray image; executing a stereo reconstruction based on the determined locations of the first point as corresponding landmark for obtaining a 3D position of the first point; executing a stereo reconstruction based on the determined locations of the second point as a corresponding landmark for obtaining a 3D position of the second point; determining the distance between the first point and the second point from the 3D position of the first point and the 3D position of the second point. In this case the first relative positioning and the second relative positioning are shifted in relation to one another in parallel to a central beam of the x-ray device.

This aspect can be preferred if it is possible to record the first and second point with one field of view of the x-ray device, i.e. when both the first and also the second x-ray image contain both the first and also the second point.

Techniques and embodiments which have been discussed in relation to the aspects described above are especially able to be combined and interchanged. Thus especially the techniques of 2D-2D image registration discussed and the determination of intrinsic and extrinsic camera parameters can also be applied to the aspect presently being discussed.

In accordance with a further aspect the invention relates to an x-ray device with an x-ray source and an x-ray detector. The x-ray device comprises an imaging controller which is configured to perform the following steps: Recording a first x-ray image which contains the first point at a first relative positioning of an x-ray source in relation to the object under examination; and recording a second x-ray image which contains the first point at a second relative positioning of an x-ray source in relation to the object under examination; and recording a third x-ray image which contains the second point at a third relative positioning of an x-ray source in relation to the object under examination; and recording a fourth x-ray image which contains the second point at a fourth relative positioning of an x-ray source in relation to the object under examination. The x-ray device further comprises a processor which is configured to perform the following steps: determining a location of the first point in the first x-ray image and in the second x-ray image; determining a location of the second point in the third x-ray image and in the fourth x-ray image; carrying out a stereo reconstruction based on the determined locations of the first point as a corresponding landmark for obtaining a 3D position of the first point; carrying out a stereo reconstruction based on the specific locations of the second point as a corresponding landmark for obtaining a 3D position of the second point; determining the distance between the first point and the second point from the 3D position of the first point and the 3D position of the second point. The first relative positioning and the second relative positioning are essentially offset in relation to one another in parallel to the central beam of the x-ray device. The third relative positioning in the fourth relative positioning are essentially offset in relation to another in parallel to the central beam of the x-ray device.

The x-ray device can be configured for carrying out a method for determining the distance in accordance with the further aspects of the invention.

For such an x-ray device effects can be obtained which are comparable with the effects which can be achieved for a method for determining the distance in accordance with a further aspect of the invention.

Other features which are considered as characteristic for the invention are set forth in the appended claims.

Naturally the features of the previously described embodiments and aspects of the invention can be combined with one another. In particular the features can be used not only in the described combinations but also in other combinations or can be used per se, without departing from the field of the invention. That is, although the invention is illustrated and described herein as embodied in the context of an x-ray process and an x-ray device, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings. In the drawing figures, the same reference characters refer to the same or similar elements.

BRIEF DESCRIPTION OF THE SEVERAL VIEWS OF THE DRAWING

FIG. 3 is a side view of the object under examination of FIG. 2 and illustrates the dimensions thereof in a longitudinal direction.

FIG. 4 (illustrated in partial views FIGS. 4A, 4B) is a flow diagram of an inventive method for determining a distance between the first and second point on the object under examination.

DETAILED DESCRIPTION OF THE INVENTION

With the subsequent figures techniques are illustrated which allow the determination of a 3D distance between a first and a second point on an object under examination. By taking into account the 3D coordinates of the points the distance can in particular be determined with an especially high accuracy. This can for example reduce the error of the physical measurement variable "distance" and can thus be of great technical relevance.

Figure 1:
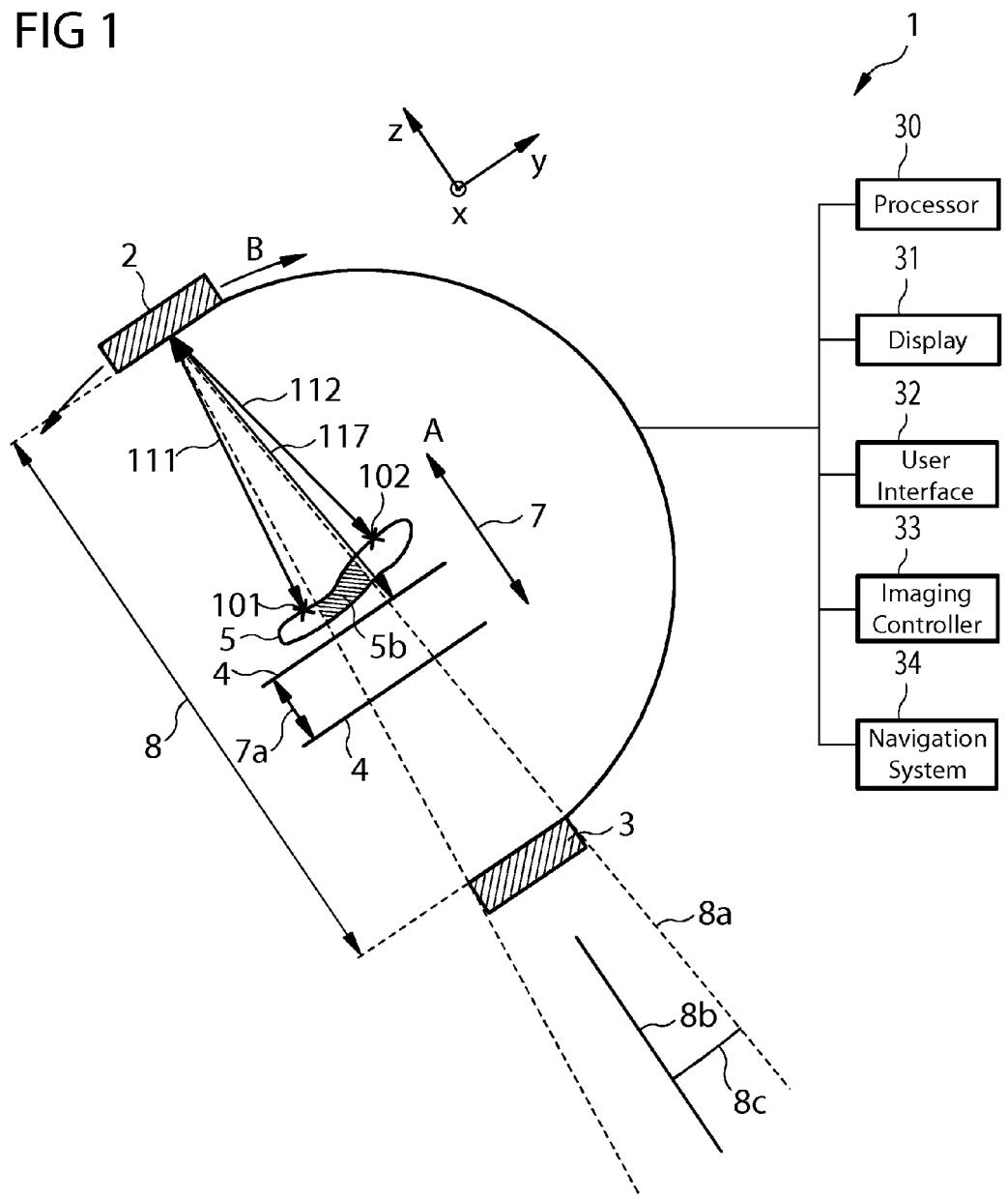
FIG. 1 schematically illustrates a C-arm device as an inventive x-ray device with an x-ray source and an x-ray detector and the beam path of x-ray photons, wherein the C-arm device is suitably usable for the method according to the invention.

Referring now to the figures of the drawing in detail and first, particularly, to FIG. 1 thereof, there is shown a schematic illustration of a C-arm device 1 with an x-ray source 2 and an x-ray detector 3. A beam path 8a of x-ray photons, which is emitted from the x-ray source 2, is indicated by dashed lines. A center of the beam path 8a defines a z-axis or longitudinal direction A, which is parallel to a central beam 8b of the x-ray photons. The central beam 8b (indicated in FIG. 1 by a solid line) can for example be perpendicular to a detector plane of the x-ray detector 3. A cross section of the beam path 8a, i.e. in an xy plane, increases for increasing distances to the x-ray source 2. This is described by the opening angle 8c of the beam path 8a. A focal length 8 designates the distance between the x-ray detector 3 and the x-ray source 2.

An object under examination 5 is located at least partly in the beam path 8a. The object under examination 5 can be a human bone for example.

The C-arm device 1 includes an imaging controller 33 which is configured for recording x-ray images of the object under examination 5 by means of suitable activation of the x-ray source 2 and the x-ray detector 3. The C-arm device 1 also includes a user interface 32, which can make it possible for a user of the C-arm device 1 to change different operating properties and parameters. In addition the C-arm device 1 includes a display 31 which is configured to optionally display an x-ray image recorded by the imaging controller 33 to the user. The C-arm device 1 further comprises an x-ray device navigation system 34 which allows a positioning of the x-ray detector 3 and the x-ray source 2, for instance in the Cartesian x-y-z coordinate system or another reference coordinate system. The C-arm device 1 further includes a processor 30 which is configured for carrying out specific calculations, e.g. distance calculations and/or image mosaic techniques, based on the x-ray images recorded by the imaging controller. The wide diversity of ways in which the processor 30 can function is described in greater detail below.

The x-ray images can be used for producing images of the object under examination 5. As can be seen from FIG. 1, the focal length 8 (or the opening angle 8a or the detector surface of the x-ray detector 3) can be insufficient to record an image of the entire object under examination 5 with a single x-ray image. It is then possible that only a part area 5b of the object under examination 5 (shown by a dashed outline in FIG. 1) is detected by the beam path 8a and recorded as such in the x-ray image.

In particular the object under examination 5 is disposed in the longitudinal direction A in parallel to the central beam 8b in the beam path 8a such that, at a first point 101 it is at a first distance 111 from the x-ray source 2 and at a second point 102 it is at a second distance 112 (the distances 111, 112 can be defined for example in relation to an origin of the central beam 8b, i.e. a geometrical center of the x-ray source 2 for example). Typically the distance between the x-ray source 2 and the x-ray detector 3 is predetermined by the construction of the unit, so that the distances 111, 112 in each case allow direct reference to the corresponding distances between the object under examination 5 and the x-ray detector 3. However only the distance 111 between the x-ray source 2 and the object under examination 5 is referred to below, but this is not to be regarded as limiting for example.

Also disposed in the beam path 8a is a marker object with a marker plane 4 which contains a plurality of location marks (not shown in FIG. 1). The marker object 4 and the object under examination 5 are in a fixed relative arrangement in relation to one another and can for example be moved together. A distance 117 between the marker plane 4 and the x-ray source 2 is larger in the case of FIG. 1 than the distances 111, 112 between the x-ray source 2 and the object under examination 5, i.e. the marker plane 4 is placed in the beam path 8a behind the object under examination 5. However the marker plane 4 can also be placed in front of the object under examination 5.

Object under examination 5 and marker plane 4 can be shifted in the direction A, i.e. along the z-axis. It is possible to set such a specific height 7 of the object under examination 5 and the marker plane 4: the height setting 7 in this case determines the distances 111, 112, 117 by positioning in the longitudinal direction A. FIG. 1 graphically shows a difference 7a between two height settings 7, i.e. an offset in the longitudinal direction A. Those object under examination 5 and also marker plane 4 can be positioned by the height setting 7 in relation to the x-ray source 2 in the longitudinal direction, in particular the positioning can involve coupling (for reasons of clarity the marker plane 4 is only shown at two height settings in FIG. 1).

Figure 5:
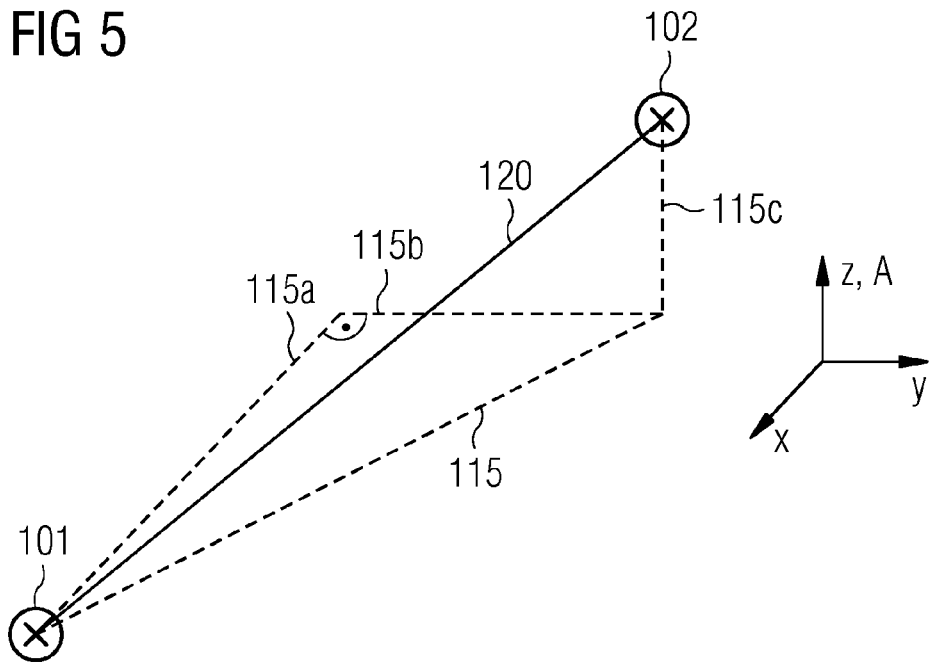
FIG. 5 illustrates the different components of the distance between the first and second points of FIG. 5 in greater detail.

Inventive techniques are explained below which allow a 3D position of the first and second point 101, 102 to be determined by means of stereo reconstruction. This enables a distance between the points 101, 102 in the 3D space to be determined, cf. FIG. 5. The distance vector or distance 120 is composed of a z-component 115c, i.e. in the longitudinal direction A, and the xy-components 115a, 115b. The xy-components 115a, 115b can for example be determined by a corresponding local encoding with the aid of the location marks 6, e.g. if the marker plane 4 lies in the xy plane. For simplicity's sake the distance vector is referred to below as the distance 120; in this case there is not only reference to the length of the vector, i.e. the length dimension, but to the entire vector size. In general the determination of the distance 120 can thus comprise the determination of the different properties of the distance vector, especially length, orientation, angle, etc.

It should be noted that it is not generally necessary for the marker plane to be at right angles to the beam path 8a. This can be preferable however. Compared to conventional techniques, such as those described at the start for example, inventive techniques can have the advantage that the z-components 115c of the distance 120 are also taken into account and a greater accuracy can be achieved through this.

Figure 2:
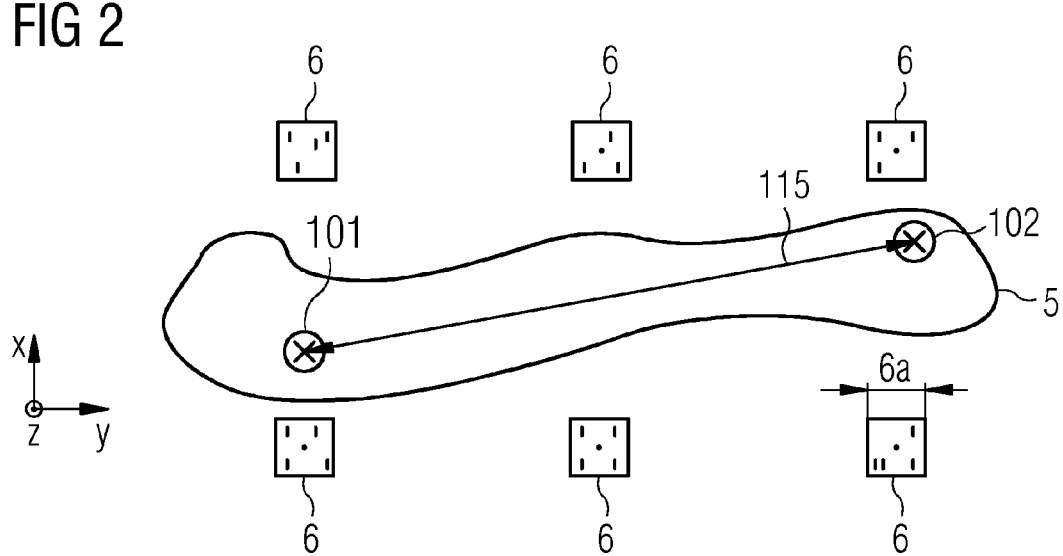
FIG. 2 is a view from above of an object under examination and location marks.

FIG. 2 is an overhead view of the object under examination 5, i.e. a view along the beam path 8a (from the viewpoint of the x-ray source 2). The dimensions of the object under examination 5 in the xy plane are therefore visible. The marker plane 4 can for example be disposed essentially in parallel to the xy plane. The location marks 6 contain e.g. a bar code or another digitally readable pattern, which contains information about an absolute position of the respective location mark 6 in the xy plane. It should be understood that from the overhead view of FIG. 2 the distances 111, 112 on the one hand and the distance 117 possibly may not be able to be determined directly. From an individual view, as is shown in FIG. 2, possibly merely one of the components 115 in the xy plane of the distance between the first and the second point 101, 102 or their projections into the marker plane 4 can be determined with the aid of the location encoding of the location marks 6.

FIG. 3 shows a side view of the object under examination 5 for two height settings 7. In FIG. 3 the two height settings 7 (cf. FIG. 1) are shown in each case from the reference system of the object under examination 5 or the marker plane 4, i.e. the x-ray source 2 shifts in relation to these objects 4, 5. This is an illustrative presentation and it should be understood that accordingly also the objects 4, 5 can be shifted in relation to the fixed-location x-ray source 2 or both the objects 4, 5, and also the x-ray source 2. The distances, etc. are only illustrated below for the two height settings 7 shown.

As can be seen from FIG. 3, different points along the y axis on the object under examination 5 are at different distances from the x-ray source 2. In particular the first distance 111 is greater than the distance 112. FIG. 3 further shows third and fourth distances 113, 114 in each case between the first point 101 and the second point 102 in relation to the marker plane 4. Also shown is a projection 101a of the first point 101 into the marker plane 4 and a projection 102a of the second point 102 into the marker plane 4. These projections can for example be offset along the beam path 8a in relation to the true position of the first and second point 101, 102. With the conventional methods described at the outset it can for example be possible to determine the distance, e.g. in the xy plane, between the projections 101a and 102a or 101b and 102b respectively.

For the two height settings 7 a first and a second x-ray image are recorded for the corresponding part area 5a of the object under examination 5, which contains the first point 101. In addition a third and a fourth x-ray image are recorded for the corresponding part area 5a of the object under examination 5 which contains the second point 102. The x-ray images also form the location marks 6 of the marker plane 4. Between the first and the second x-ray image, as well as between the third and the fourth x-ray image an imaging scale of the respective part area 5a of the object under examination 5a essentially changes. This is illustrated in greater detail in FIG. 6.

Figure 6:
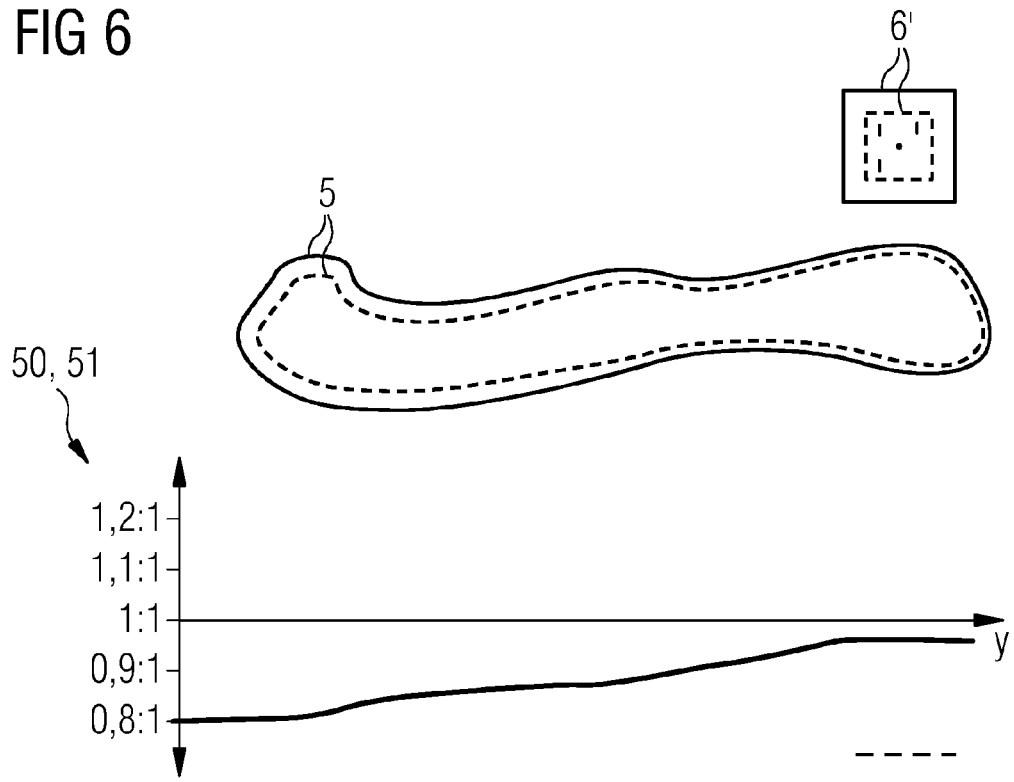
FIG. 6 is a view from above in accordance with FIG. 2 onto the object under examination and illustrates a scaling factor of the object under examination and the location marks between two x-ray images with different height settings of the C-arm device.

At the top of FIG. 6 a view (in accordance with FIG. 2) of the object under examination 5 and a location mark 6 is illustrated for two different height settings 7 of the C-arm device 1 with a solid line and a dashed line respectively. As can be seen from FIG. 6, the imaging size changes as a function of the height setting 7 because of the increasing cross section of the beam path 8a (diverging beam). The topography of the object under examination 5 additionally means that the scaling factor, i.e. the ratio of the imaging scales between the two height settings 7 changes.

Shown at the bottom of FIG. 6 is the scaling factor 50 (solid line) of the object under examination 5 or the further scaling factor 51 (dashed line) of the location marks 6. The location marks 6 have a dimension 6a. This can especially be known. Since information about the further scaling factor 51 of the location marks 6 is only available in the y direction in a restricted area in the y direction in the marker plane 4, the further scaling factor 51 can only be determined or defined in this area. In particular the scaling factors 50, 51 can be determined locally-resolved in a 2D-2D image registration of the first and second x-ray images.

Such a 2D-2D image registration is also carried out in order to determine the locations of the points 101, 102 in the first and second or third and fourth x-ray image respectively. As an alternative a user can manually determine via the user interface 32 the location of points 101, 102 in the two pairs of x-ray images. Intrinsic and extrinsic camera parameters can additionally be determined for the stereo reconstruction, which is explained below.

Based on the first and second x-ray image, as well as on the third and fourth x-ray image, a stereo reconstruction, as is known to the person skilled in the art, of the first point 101 as well as of the second point 102 can be carried out. Since for example only one different height setting 7 advantageously lies between the respectively registered x-ray images, only the imaging scale can be different for example. This can make an especially precise and reliable 2D-2D image registration possible. This enables a 3D position of the points 101, 102 to be determined, e.g. in relation to the marker plane 4 or the x-ray source 2. From this the distance 120 can be calculated, by means of conventional vector geometry for example.

The corresponding techniques are shown in the flow diagram of FIG. 4. The method begins with step S1. Initially, in step S2, the intrinsic camera parameters of the C-arm device 1 are determined. The intrinsic camera parameters can be read out for example in step S2 from a memory; the intrinsic camera parameters can namely e.g. be predetermined for the specific C-arm device 1. The calibration can then have been undertaken at a specific earlier point in time.

It is also possible to perform updated calibration. For this purpose two or more calibration x-ray images can be recorded which map the location marks 6 from different perspectives. For this purpose the marker plane 4 can be recorded with different orientations of the x-ray source 2. Techniques are then known to the person skilled in the art for determining the intrinsic camera parameters from the calibration images.

Then in a step S3 the object under examination 5 is placed in the beam path 8a. The marker plane 4 is located in the beam path in front of or behind the object under examination 5. The relative distance between the marker plane 4 and the object under examination 5 can be fixed.

In step S4 the positioning of the C-arm device 1 is undertaken, primarily in the xy plane, e.g. by repositioning in the direction B or by shifting the entire C-arm in relation to a first part area 5a of the object under examination 5. For example the object under examination 5 (with marker plane 4) can be shifted. In addition or as an alternative the x-ray source 2 and the x-ray detector 3 can also be moved. The positioning in step S4 is carried out for example so that a distal or proximal end or any other relevant anatomical area of the object under examination 5 comes to rest in the beam path 8a. The effect of this can be that the first point 101 is contained in the x-ray images subsequently recorded (see steps S5 and S7), even if its location is not yet precisely determined.

The positioning in step S4 leads to a first relative positioning. This first relative positioning is also characterized by a certain height setting 7.

In step S5 the first x-ray image is recorded with the first relative positioning.

In step S6 the arm is positioned to reach a different (in relation to the first relative positioning) height setting 7. For this purpose the object under examination 5 is shifted with marker plane 4 and/or the x-ray source 2 with x-ray detector 3 in the longitudinal direction A, i.e. in parallel to the central beam 8b.

In step S7 the second x-ray image is detected for the second relative positioning. Both the first x-ray image and also the second x-ray image map the first part area 5a and the first point 101.

In steps S8 and S9 the extrinsic camera parameters are determined in each case for the first and the second x-ray image from step S5 and S7. For this purpose for example the pose of the x-ray source for the first and second relative positioning can be determined by means of the navigation device 34 for example, see FIG. 1. As an alternative or in addition it is also possible to compute the pose of the x-ray source 2 from the location marks 6 mapped in the first and second x-ray images. This is possible since the absolute positioning can be obtained from the local encoding of the location marks.

In step S10 it is decided whether an automatic assignment of the first point 101 as corresponding landmark in the first and second x-ray image is to be undertaken. For an automatic assignment in step S11 the 2D-2D image registration is carried out. From the 2D-2D image registration a plurality of points, especially also the first point 101, are identified as corresponding landmarks by determining the transformation between the first and second x-ray image. Since between the first and second x-ray image only a positioning in the longitudinal direction of the first and second relative positioning has changed, i.e. the object under examination 5 was merely shifted in parallel to the central beam 8b, the mapping scale primarily changes. This is characteristic for the corresponding x-ray imaging by means of the C-arm device 1. Therefore the transformation determined by the 2D-2D image registration will primarily involve the scaling factor 50; rotation and compression/distortion, etc. are comparatively small. This can result in a high certainty (confidence) or high accuracy of the 2D-2D image registration so that the corresponding landmarks can be found reliably with few errors. This can cause a slight error in the subsequent determination of the distance (see below, step S15). The user can optionally in step S11 click on point 1 in the first or the second x-ray image or an image recognition and analysis routine can identify a relevant point, such as the proximal or distal end, automatically on the basis of the anatomy of the object under examination 5.

As an alternative in step S12 the first point 101 can be manually marked by the user, e.g. clicked on, in the first and also second x-ray image.

In step S13 the stereo reconstruction delivers the 3D position of the first point 101. The 3D position corresponds to an arrangement of the point in the 3D space, e.g. in relation to the reference coordination system (e.g. in relation to the C-arm device 1 and/or the marker plane 4). The stereo reconstruction is carried out based on the intrinsic and extrinsic camera parameters from steps S2 and S8, S9.

In step S14 a check is made as to whether a further part area 5a is to be recorded. If for example only distances 120 between first and second points 101, 102 are to be determined, which are already mapped by the first and the second x-ray image from step S5 and S7, this can already be done directly (simply by recording third, fourth, etc. x-ray images) in step S15. Otherwise the steps S4-S13 can be carried out again for a further part area 5a or for third and fourth x-ray images.

In step S15 distances between the 3D positions of corresponding points are determined. These points can for example be the points marked in steps S11 or S12 or, especially in the event of a 2D-2D image registration carried out in step S11, it can be possible for the user in step S15 to determine relevant points by means of the user interface 32. The corresponding landmarks are then already defined from the 2D-2D image registration.

It should be understood that a sequence of execution of the steps can be varied. Thus for example step S8 can be carried out before step S7 or step S2 only within the framework of and/or based on the recording of the first and second x-ray image in steps S5 and S7.

Although the invention has been illustrated in greater detail and described by the preferred exemplary embodiments, the invention is not restricted by the disclosed examples and other variations can be derived herefrom by the person skilled in the art, without departing from the scope of the invention.

Thus, in relation to the figures, the reader is especially primarily referred to a C-arm device as the x-ray system. However this is not limiting and corresponding techniques and effects can also be applied and obtained for other x-ray devices, e.g. fixed x-ray devices. In particular corresponding techniques can also be used for other imaging techniques; in particular in relation to such techniques which feature an imaging scale which is dependent on a distance to a detector plane, i.e. possess a divergent beam path.

Reference is also primarily made to such forms of embodiment and aspects of the invention in which separate first and second or respectively third and fourth part areas 5a of the object under examination 5 are recorded. But it should be understood that in accordance with the invention the recording of only one pair of x-rays, i.e. the first and second x-ray image, can be sufficient if these already contain the first and second point 101, 102.

THE FOLLOWING IS A LIST OF REFERENCE
CHARACTERS USED IN THE DESCRIPTION

1 C-arm device
2 X-ray source
3 X-ray detector
4 Marker plane
5 Object
5a Object plane
5b Part area
6 Location mark
6a Lateral dimensions of the location mark
7 Height adjustment
7a Difference of the height adjustment
8 Focal length
8a Beam path
8b Central beam
8c Opening angle
9a Distance
9b Further distance
A Adjustment in longitudinal direction
B Adjustment with orbital rotation
30 Processor
31 Display
32 User interface
33 Imaging controller
34 Navigation system
50 Scaling factor
51 Further scaling factor
101 First point
101a,b Projection of first point
102 Second point
102a,b Projection of second point
111 First distance
112 Second distance
113 Third of distance
114 Fourth distance
115 Distance in the xy plane
115a x component distance
115b y component distance
115c z component distance
117 Distance
120 Distance
S1-S10 Step

The invention claimed is:

1. A method for determining a distance between a first point and a second point on an object under examination within the body of a person under examination by x-ray imaging with an x-ray device, the method which comprises:
   recording a first x-ray image containing the first point, with a first relative positioning of an x-ray source to the object under examination;
   recording a second x-ray image containing the first point, with a second relative positioning of the x-ray source to the object under examination;
   wherein the first relative positioning and the second relative positioning are shifted relative to one another substantially in parallel to a central beam of the x-ray device;
   recording a third x-ray image containing the second point, with a third relative positioning of the x-ray source to the object under examination;
   recording a fourth x-ray image containing the second point, with a fourth relative positioning of the x-ray source to the object under examination;
   wherein the third relative positioning and the fourth relative positioning are shifted relative to one another substantially in parallel to the central beam of the x-ray device;
   determining a location of the first point in the first x-ray image and in the second x-ray image;
   determining a location of the second point in the third x-ray image and in the fourth x-ray image;
   carrying out a stereo reconstruction based on the locations of the first point thus determined as a corresponding landmark for obtaining a 3D position of the first point;
   carrying out a stereo reconstruction based on the locations of the second point thus determined as a corresponding landmark for obtaining a 3D position of the second point; and
   determining the distance between the first point and the second point from the 3D position of the first point and the 3D position of the second point.

2. The method according to claim 1, wherein the first and second relative positioning and the third and fourth relative positioning are respectively shifted relative to one another at right angles to the central beam of the x-ray device.

3. The method according to claim 1, wherein:
the first x-ray image and the second x-ray image record an image of a first partial area of the object under examination and have mutually different imaging scales and/or are not, or only slightly, rotated and tilted in relation to one another; and
the third x-ray image and the fourth x-ray image record an image of a second partial area of the object under examination and have mutually different imaging scales and/or are not, or only slightly, rotated and tilted in relation to one another.

4. The method according to claim 1, wherein the step of determining the locations of the first point and the step of determining the locations of the second point are manual steps carried out manually by a user of the x-ray device.

5. The method according to claim 1, wherein the step of determining the locations of the first point and the step of determining the locations of the second point are carried out at least partly automatically by a 2D-2D image registration of the first x-ray image with the second x-ray image and also of the third x-ray image with the fourth x-ray image.

6. The method according to claim 1, further comprising:
determining extrinsic camera parameters for the stereo reconstruction, which describe a 3D position and an orientation of the x-ray source in the first and second and the third and fourth relative positionings; and
wherein an execution of the stereo reconstruction takes account of the extrinsic camera parameters.

7. The method according to claim 6, wherein:
each of the first and the second and the third and the fourth x-ray image maps location marks of a location-coded marker plane; and
the extrinsic camera parameters are determined based on the mapped location marks.

8. The method according to claim 7, wherein the marker plane is defined to substantially extend orthogonally to a central beam of the x-ray device.

9. The method according to claim 6, which comprises determining the extrinsic camera parameters based on a monitoring of a positioning of the x-ray device between the different relative positionings.

10. The method according to claim 1, which further comprises:
recording at least two calibration x-ray images, which each map location marks of a location-encoded marker plane, wherein the at least two calibration x-ray images are recorded with different orientations of the x-ray source to the marker plane; and
determining intrinsic camera parameters for the stereo reconstruction, which describe imaging characteristics of the x-ray device, from the calibration x-ray images based on the mapped location marks;
wherein a execution of the stereo reconstruction takes account of the intrinsic camera parameters.

11. The method according to claim 10, wherein at least one of at least two calibration x-ray images is the first x-ray image and/or the second x-ray image and/or the third x-ray image and/or the fourth x-ray image.

12. An x-ray device, comprising:
an x-ray source and an x-ray detector;
an imaging controller configured for carrying out the following steps:
recording a first x-ray image containing a first point in an object under examination, with a first relative positioning of an x-ray source to the object under examination;
recording a second x-ray image containing the first point, with a second relative positioning of the x-ray source to the object under examination;
recording a third x-ray image containing a second point in an object under examination, with a third relative positioning of the x-ray source to the object under examination;
recording a fourth x-ray image containing the second point, with a fourth relative positioning of the x-ray source to the object under examination;
wherein the first relative positioning and the second relative positioning are shifted relative to one another substantially in parallel to a central beam of the x-ray device; and
wherein the third relative positioning and the fourth relative positioning are shifted relative to one another substantially in parallel to the central beam of the x-ray device; and
a processor configured for carrying out the following steps:
determining a location of the first point in the first x-ray image and in the second x-ray image;
determining a location of the second point in the third x-ray image and the fourth x-ray image;
carrying out a stereo reconstruction based on the determined locations of the first point as corresponding landmark for obtaining a 3D position of the first point;
carrying out a stereo reconstruction based on the determined locations of the second point as corresponding landmark for obtaining a 3D position of the second point;
determining a distance between the first point and the second point from the 3D position of the first point and the 3D position of the second point.

* * * * *